United States Patent [19]

Burgoyne, Jr. et al.

[11] Patent Number: 4,556,546
[45] Date of Patent: Dec. 3, 1985

[54] BIS TERTIARY AMINO ALKYL DERIVATIVES AS SOLVENTS FOR ACID GAS REMOVAL FROM GAS STREAMS

[75] Inventors: William F. Burgoyne, Jr., Allentown; Michael S. Chen, Zionsville; Dale D. Dixon, Kutztown; Thomas J. Edwards, Allentown, all of Pa.

[73] Assignee: Air Products and Chemicals, Inc., Allentown, Pa.

[21] Appl. No.: 640,500

[22] Filed: Aug. 14, 1984

Related U.S. Application Data

[63] Continuation-in-part of Ser. No. 491,506, May 4, 1983, abandoned.

[51] Int. Cl.$^4$ ............................................. B01D 53/34
[52] U.S. Cl. ..................................... 423/226; 423/224; 423/228; 423/229; 423/243; 423/563; 55/68; 55/73
[58] Field of Search .............. 423/224, 226, 228, 229, 423/243; 55/68, 73

[56] References Cited

U.S. PATENT DOCUMENTS

| | | | |
|---|---|---|---|
| 1,951,992 | 3/1934 | Perkins | 423/228 |
| 2,083,213 | 6/1937 | Baehr et al. | 423/228 |
| 3,516,793 | 6/1970 | Renault | 423/225 |
| 3,555,782 | 1/1971 | Deringer | 55/48 |
| 3,645,925 | 2/1972 | Speranza et al. | 521/115 |
| 3,661,808 | 5/1972 | Kennedy | 521/115 |
| 4,094,957 | 6/1978 | Sartori et al. | 423/228 X |
| 4,100,256 | 7/1978 | Bozzelli et al. | 423/220 |
| 4,112,049 | 9/1978 | Bozzelli et al. | 423/226 |
| 4,405,582 | 9/1983 | Stogryn et al. | 423/228 X |

FOREIGN PATENT DOCUMENTS 0008449 8/1979 European Pat. Off. ............... 53/34

*Primary Examiner*—John Doll
*Assistant Examiner*—Jackson Leeds
*Attorney, Agent, or Firm*—Geoffrey L. Chase; E. Eugene Innis; James C. Simmons

[57] ABSTRACT

A process is set forth for the selective removal of acid gases such as $H_2S$, COS and $CO_2$ from a gas stream by contacting the stream with a bis tertiary amino alkyl solvent compound such as 4,4'-(oxydi-2,1-ethanediyl) bismorpholine. When used in an aqueous solution, the compounds catalytically hydrolyze COS to $H_2S$ and $CO_2$.

10 Claims, No Drawings

BIS TERTIARY AMINO ALKYL DERIVATIVES AS SOLVENTS FOR ACID GAS REMOVAL FROM GAS STREAMS

CROSS REFERENCE TO RELATED APPLICATION

This is a continuation-in-part of U.S. Application Ser. No. 491,506 filed May 4, 1983 now abandoned.

TECHNICAL FIELD

This invention relates to a process for selectively removing acid gas components from a gas stream utilizing bis tertiary amino alkyl derivatives. More specifically, the invention is related to a process for selectively removing acid gas components from a gas stream by the catalytic hydrolysis of COS and the absorption of other acid gas components in an aqueous solution of such a derivative.

BACKGROUND OF THE PRIOR ART

Industrial gas streams, such as refinery gas streams, natural gas streams, synthesis gas streams, coal gas streams and other such streams generally contain varying amounts of acid gas components. The usual acid gas components are sulfur compounds such as hydrogen sulfide, carbonyl sulfide, carbon disulfide and various alkyl sulfur compounds such as mercaptans. Additionally, carbon dioxide which is considered an acid gas is generally present in such industrial gas streams. Such acid gases are further defined in U.S. Pat. No. 4,094,957, incorporated herein by reference. All of these gas streams are detrimental to the value of the industrial gas stream and in addition, are corrosive to transport equipment and the general environment in which the industrial gases are used. Restrictions have been placed upon the content of acid gas components in industrial gas streams both by the industry and by the government concerned with environmental and atmospheric pollution. Therefore, it has been a long term objective of the industry, to successfully separate and remove acid gas components from the various industrial gas streams in which such components inherently form at least some not insubstantial concentration of the overall gas composition. The prior art has utilized both chemical sorbing materials and physical sorbing materials in efforts to economically remove the acid gas components from industrial gas streams. Alkanolamines have been utilized for the selective removal of acid gas components from various gas streams. Such amines have been utilized with various inorganic components such as inorganic bases for enhanced separation or extraction of acid gas components from gas streams.

The prior art has used various amine compounds for acid gas absorption as in U.S. Pat. No. 1,951,992, but the compounds of that disclosure do not have the tertiary amine and ether linkages of the compounds of the present invention.

In U.S. Pat. No. 2,083,213, hydrogen sulfide is recovered using primary and secondary amines which do not have any ether functionality. Such compounds will operate in a chemical absorption manner with problems of capacity and regeneration.

The prior art has also utilized cyclic nitrogen compounds for the removal of acid gas components from gas streams. In U.S. Pat. No. 3,555,782, morpholine or a C-substituted morpholine is utilized as an acid gas component extraction medium for stripping such components from a gas stream. Specifically, 2-methyl, 2-ethyl, 2-propyl or 2-butyl morpholine are contemplated for acid gas removal. Non-alkyl substituents may also be utilized such as 2-ketomorpholine. However, it is stated that N-substituted morpholines are not particularly effective for the purpose of the invention.

In U.S. Pat. No. 3,516,793, alkanolamines or morpholines are used in conjunction with the monoalkyl ether of a polyhydric alcohol to absorb hydrogen sulfide from a gas stream. Morpholine is preferred to the substituted forms, such as morpholine ethanol, morpholine ethanol ethyl ether and morpholine phenyl.

U.S. Pat. No. 4,094,957 discloses various tertiary amines used in the treatment of acid gases as activators for chemical absorbents of alkali salts and hydroxides. Combinations of tertiary amine and ether functionality are not set forth.

The hydrolysis of acid components such as carbonyl sulfide are known to be catalyzed by piperazinone and alkyl-substituted piperazinones as set forth in U.S. Pat. No. 4,100,256.

Selective extraction of hydrogen sulfide and lower alkyl mercaptans with piperazinone or alkyl-substituted piperazinone is also known in the prior art as suggested by U.S. Pat. No. 4,112,049. This patent recites that additionally alkanolamines and morpholine derivatives, such as N-methyl-3-morpholinone are known sour gas purification solvents.

The use of morpholines and piperazines as hydrolysis catalysts for carbonyl sulfide is also set forth in European patent application No. 0 008 449.

BRIEF SUMMARY OF THE INVENTION

The present invention constitutes a process for purifying gas streams of acid gas components, such as $H_2S$, COS and $CO_2$, comprising contacting the gas stream with an acid gas absorbing solvent compound selected from the group having the formula

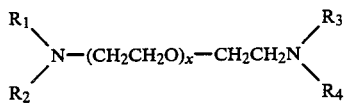

where $x = 1, 2$ or $3$
where $R_{1-4}$ = individually lower alkyl which is $C_1$ to $C_4$ normal or branched hydrocarbons or $R_1 + R_2$ and/or $R_3 + R_4$ can constitute a cyclic derivative from the group

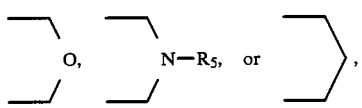

wherein $R_5$ is a lower alkyl $C_1$ to $C_4$ normal or branched hydrocarbon, so as to absorb a predominant amount of such acid gas components from said gas stream. The bis tertiary amino alkyl derivative may be utilized in an ahydrous condition as a selective solvent for removing the acid gas components from a gas stream or more advantageously, the derivative can be utilized in an aqueous solution to not only selectively extract acid gas components in general, but specifically catalytically hydrolyze the COS to $H_2S$ and $CO_2$. Alternately, the solvent can be in solution with other solvents or vehicles as an absorbing solution.

Preferably, the absorbing solution of the derivative is in an aqueous solution wherein the bis tertiary amino alkyl compound is 30–99.5 wt% of the solution.

Preferably, the absorption of acid gas components with the absorbing solution of the derivative is conducted at a temperature in the range of 0° to 100° C.

It is preferred to operate the absorption process at a pressure in the range of 50 to 1000 psia.

Preferably the derivative is 4,4'-(oxydi-2,1-ethanediyl)bismorpholine. Alternately, the derivative is 4,4'-(oxydi-2,1-ethanediyl)bismorpholine with a viscosity reducing effective amount of 2-[2-(4-morpholinyl)ethoxy]ethanol.

DETAILED DESCRIPTION OF THE INVENTION

The use of bis tertiary amino alkyl compounds or derivatives as solvents for acid gases has been shown to be particularly effective for the removal of sulfur compounds such as hydrogen sulfide and carbonyl sulfide preferentially over carbon dioxide. This type of selective removal is particularly important to the processing of synthesis gases. The morpholine compounds of the subject structure are of particular interest. These solvents extract acid gas components from gas streams in the manner of physical solvents. This means that the solvents may be utilized for bulk removal of components from a gas stream at high pressures. It also means that the solvents can absorb acid gas components with low heats of absorption. Finally, the characteristics of these solvents as physical solvents means that regeneration can be performed simply and with a minimum of energy consumption. However, these solvents also exhibit selectivities for sulfur compounds similar to known prior art chemical solvents.

Another attribute of the presently contemplated solvents is their ability to catalytically hydrolyze carbonyl sulfide when the solvent is used in an aqueous solution. When carbonyl sulfide is hydrolyzed, the end products are carbon dioxide and hydrogen sulfide. In catalytically hydrolyzing carbonyl sulfide to these end products, the solvents of the present invention are not detrimentally consumed as a reactant would be and yet any contained carbonyl sulfide is transformed into the acid gas components, hydrogen sulfide and carbon dioxide, which are more readily differentially extracted one from another. The solvents of the present invention may be utilized for the purification of natural gas for pipelining, the purification of synthesis gas or the upgrading of oil/coal conversion process products for further use of the resulting gas in ammonia, urea or methanol plants. The tertiary amine functionality of the compounds of the invention provides the physical absorbent capability without the capacity and regeneration limitations of the chemically operating primary and secondary amines. The ether functionality provides good $CO_2$ and $H_2S$ absorption, while enhancing the basicity of the overall compounds of the invention.

The solvents of the present invention can be effectively used in their pure forms or as mixtures with other solvents or water. When utilized with water, the solvents have the additional benefit of hydrolyzing carbonyl sulfide acid gas components to hydrogen sulfide and carbon dioxide. Various additional solvents may be added to increase the physical solvent characteristic of the present solvent or alternately increase the chemical solvent characteristics of the present solvents. Additionally, other solvent components or vehicles may be mixed with the present solvents in order to adjust the overall molecular weight distribution or the viscosity of the solvent system.

Although bis tertiary amino alkyl compounds are generally within the contemplation of the present invention, specific compounds contemplated for utilization as acid gas solvents in the process of the present invention preferably include N,N-dimethyl-4-morpholine ethanamine, 2,2'-oxybis(N,N-dimethylethanamine, N,N-dimethyl-2-[2(4-morpholinyl)ethoxy]ethanamine, and 4,4'-(oxydi-2,1-ethanediyl) bismorpholine. The latter compound is the most preferred solvent component. It is recited in U.S. Pat. No. 3,645,925 and U.S. Pat. No. 3,661,808 hereby incorporated herein by reference. A particularly appropriate solvent mixture comprises 4,4'-(oxydi-2,1-ethanediyl)bismorpholine with a minor amount of 2-[2-(4-morpholinyl)ethoxy]ethanol as a viscosity reductant in an aqueous solution. This solvent mixture is particularly appropriate for providing a preferred viscosity solvent which catalytically hydrolyzes carbonyl sulfide.

These compounds and their structures are set forth below, however it is understood that other compounds having the same basic structure and the necessary tertiary amine and ether functionalities would be contemplated as efficacious components of the invention:

(a) 4,4'-(oxydi-2,1-ethanediyl)bismorpholine also known as 4,4'-(oxydiethylene)dimorpholine and 4,4'-dimorpholinodiethyl ether and bis(2-morpholino ethyl)ether.

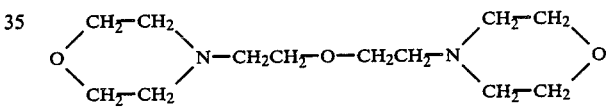

(b) 2-[2(4-morpholinyl)ethoxy]ethanol also known as 2-(2-morpholinoethoxy)ethanol.

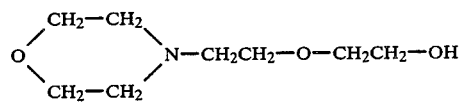

(c) N,N-dimethyl-4-morpholineethanamine also known as 4-[2-(dimethylamino)ethyl]morpholine.

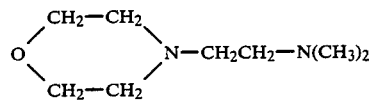

(d) 2,2'-oxybis(N,N-dimethylethanamine) also known as 2,2'-oxybis(N,N-dimethylethylamine).

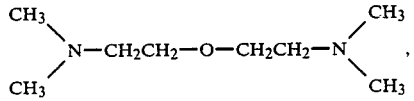

(e) N,N-dimethyl-2-[2-(4-morpholinyl)ethoxy]ethanamine also known as 2-[dimethylamino]ethyl-2-(4-morpholinyl)ethyl ether.

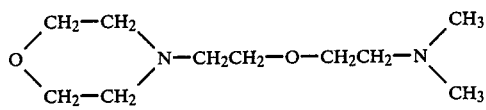

The solvent or solvent mixtures of the present invention can be utilized in any of the known absorption-desorption recycle acid gas removal schemes which are presently practiced for the purification of a synthesis gas or a natural gas. More specifically, the solvent or solvent mixtures of the present invention would be contemplated for countercurrent contact with the acid gas containing fuel stream in a contact tower or column. The solvent containing sulfur compounds and carbon dioxide would be removed usually from the bottom of the column while the purified fuel gas stream is removed from the overhead of the column. The solvent can then be regenerated by a rapid reduction in pressure, such as flashing, by stripping with inert gas or by the heating of the rich solvent or a combination of such treatments. The extracted sulfur compounds can constitute a feed for a Claus plant. The regenerated solvent can then be recycled to the scrubbing column. More than one contact of the fuel gas with such solvent or solvent mixtures can be contemplated particularly if the acid gas content of the fuel gas stream is high. This brief description of the utility of the present solvents is not deemed to be a detailed teaching of how the solvents or solvent mixtures can be used, but such processes and flow schemes are well known in the prior art for physical and chemical solvents.

The bis tertiary amino alkyl solvents of the present invention are particularly pertinent for acid gas removal utilities where acid gases must be removed to trace levels with a minimum of energy input or regeneration. In addition, when synthesis gas is being treated, an appreciable amount of carbonyl sulfide can be present, and the sorption selectivities of carbonyl sulfide versus carbon dioxide are not appreciably different. Therefore the removal of carbonyl sulfide to trace levels has in the past entailed absorbing large quantities of carbon dioxide. Previously known physical solvents, such as Selexol, Rectisol or propylene carbonate, are generally used for bulk removal of acid gas components. They absorb acid gases by intermolecular attractions without chemical reaction. Their heats of absorption are usually low. However, their inability to economically remove acid gases to trace levels is widely recognized. On the other hand, chemical solvents, such as aqueous solutions of primary and secondary amines, are primarily chosen for their removal of acid gases at low partial pressures, for instance for trimming or polishing operations where they absorb acid gases by chemical reaction stoichiometrically. They are impractical to use for bulk acid gas removal. In addition, their heats of reaction are substantially higher than physical solvents, and the energy required for regeneration can be substantial. A compromise between the properties of chemical and physical solvents has been practiced by the utilization of mixed solvents. Mixed solvents usually comprise a homogeneous mixture of chemical and physical solvents. Such physical and chemical solvent mixtures provide a compromise of abilities and detriments in the removal of acid gas components from fuel gas streams.

The present solvents comprising bis tertiary amino alkyl compounds overcome the disadvantages of the physical and chemical solvents of the prior art and the problem of co-absorption of carbon dioxide and carbonyl sulfide. These bis tertiary amino alkyl solvents provide bulk acid gas removal capabilities similar to other physical solvents, while at the same time removing acid gases to trace levels. The trace level removal is benefited by the ability of the present solvents to catalytically hydrolyze carbonyl sulfide to hydrogen sulfide and carbon dioxide when the solvent is in the presence of water.

High concentrations of carbonyl sulfide are generally present in synthesis gas fuel processes. Removal of carbonyl sulfide by chemical solvents is particularly troublesome because the primary and secondary amines which constitute the predominent chemical solvents form relatively stable thiocarbonates with carbonyl sulfide. The general solution to the removal of carbonyl sulfide has been to pass the gas stream to be processed over a separate bed for the hydrolysis of carbonyl sulfide to hydrogen sulfide and carbon dioxide. For instance the use of alumina beads in an absorber bed has been the practice of the prior art. Such an additional piece of apparatus or stage in a process constitutes a cost penalty in terms of processing power requirements and to capital investment.

The compounds of the present invention have the following general chemical structure:

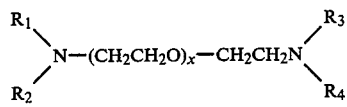

where $x = 1$, 2 or 3 and $R_{1-4}$ are individually lower alkyl which is $C_1$ to $C_4$ normal or branched hydrocarbons or $R_1 + R_2$ and/or $R_3 + R_4$ form a cyclic derivative from the group

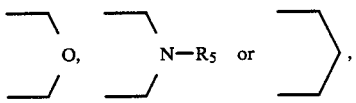

wherein $R_5$ is a lower alkyl $C_1$ to $C_4$ normal or branched hydrocarbon. These solvents of the present invention have the advantages common to most physical solvents, including the ability to effectively scrub high acid gas containing fuel gas mixtures (5 to 95% by volume acidic gas components) while providing a low solvent circulation rate and low energy consumption for regeneration. These solvents have a high selectivity for sulfur compounds (hydrogen sulfide and carbonyl sulfide) over carbon dioxide. In addition, the solvents of the present invention have catalytic activity for the hydrolysis of carbonyl sulfide to hydrogen sulfide and carbon dioxide when the solvents are present in an aqueous solution. These solvents also have a low vapor pressure over the normal scrubbing/regeneration temperature range of $-10°$ C. to $200°$ C. so that the solvent lost due to vapor pressures is low. Finally, the solvents of the present invention have low viscosities of several centipoises to tens of centipoises, such that pumping energy requirements are also low. The viscosities of the present solvents may also be improved by the use of the solvents in mixtures with lower viscosity components. For instance, 4,4′(oxidi-2,1-ethenediyl)bismorpholine may be combined with 2-[2-(4-morpholinyl)ethoxy]ethanol in order to provide a solvent mixture with optimum solvent viscosity.

The utility of the solvent process of the present invention is demonstrated by the following examples in which the preferred solvent 4,4'(oxydi-2,1-ethanediyl)-bismorpholine is compared in a number of critical solvent parameters against known acid gas solvents such as the dimethyl ether of polyethylene glycol.

EXAMPLE 1

The most important criteria for selecting an acid gas physical solvent is the solvent's capacity for the absorption of acidic gaseous components. In this example, the preferred solvent, 4,4'(oxdi-2,1-ethanediyl)bismorpholine (BMDEG) is compared against a known commercial physical solvent, dimethylether of polyethylene glycol (DMEPG) on a weight basis for the absorption of carbon dioxide. Data was collected from an apparatus which comprised four 500 ml stainless steel vessels in which pure carbon dioxide gas was sparged through a 90 micron stainless steel filter element into solvent liquid pools in said vessels at a constant temperature. After a set period of time the solvent became saturated with carbon dioxide. Liquid samples were then withdrawn from the system through valves in the vessels and delivered to an expansion vessel and a test tube from which the dissolved carbon dioxide was stripped in a flow of inert Argon gas. The stripped gas stream was analyzed by gas chromatography. The solvent capacity was then back calculated via the gas law for this analysis. The results are shown in Table 1.

TABLE 1

| $CO_2$ Solvent Capacity (lb $CO_2$ per lb of Solvent) | | BMDEG (MW = 244) | DMEPG (MW = 280) |
|---|---|---|---|
| At 55° C. | 20 psia | 0.0048 | 0.0042 |
|  | 35 | 0.0074 | 0.0072 |
|  | 55 | 0.0116 | 0.0118 |
|  | 70 | 0.0150 | 0.0152 |
| At 100° C. | 20 psia | 0.0025 | 0.0016 |
|  | 35 | 0.0045 | 0.0030 |
|  | 55 | 0.0059 | 0.0047 |
|  | 70 | 0.0068 | 0.0062 |

EXAMPLE 2

Using the same apparatus as described in Example 1 above, data was collected for the solvent capacities of 4,4'-(oxydi-2,1-ethanediyl)bismorpholine and dimethyl ether of polyethylene glycol for hydrogen sulfide. The collected data is represented in Table 2 below.

TABLE 2

| $H_2S$ solvent capacity (lb $H_2S$ per lb solvent) | | BMDEG | DMEPG |
|---|---|---|---|
| At 55° C. | 10 psia | 0.0043 | 0.0050 |
|  | 20 | 0.0183 | 0.0214 |
|  | 35 | 0.0349 | 0.0326 |
|  | 55 | 0.0570 | 0.0553 |
|  | 70 | 0.0731 | 0.0695 |
| At 100° C. | 20 psia | 0.0086 | 0.0080 |
|  | 35 | 0.0155 | 0.0147 |
|  | 55 | 0.0202 | 0.0249 |
|  | 70 | 0.0287 | 0.0341 |

EXAMPLE 3

Using the same apparatus and procedure as in Example 1 above, the solvent capacity of 4,4'(oxydi-2,1-ethanediyl)bismorpholine and the dimethyl ether of polyethylene glycol on a weight basis were compared for the absorption of carbonyl sulfide. The data is presented in Table 3 below. This example shows that the solvent of the present invention has a capacity for carbonyl sulfide at 55° C., 50 to 67% better than the known commercial solvent. Therefore, when the solvent of the present invention is used for the selective removal of sulfur compounds from a process gas it will extract such sulfur compounds more completely.

TABLE 3

| COS Solvent Capacity (lb COS per lb solvent) | | BMDEG | DMEPG |
|---|---|---|---|
| At 55° C. | 20 psia | 0.0223 | 0.0144 |
|  | 35 | 0.0417 | 0.0265 |
|  | 55 | 0.0726 | 0.0445 |
|  | 70 | 0.100 | 0.0604 |
| At 100° C. | 20 psia | 0.0102 | 0.0100 |
|  | 35 | 0.0179 | 0.0175 |
|  | 55 | 0.0295 | 0.0290 |
|  | 70 | 0.0377 | 0.0370 |

EXAMPLE 4

When a particular solvent is used to scrub raw natural gas, containing mainly methane, in order to remove the acidic gaseous components such as carbon dioxide, hydrogen sulfide and carbonyl sulfide, it is important to minimize the co-absorption of methane. Such co-absorption would represent a loss of a valuable fuel gas component. The present example was conducted in apparatus similar to that used in Example 1 above. The resulting data is tabulated in Table 4 below. Although the data indicates that the solvent of the present invention has slightly higher co-absorption of methane, within experimental error, the two solvents behaved essentially the same.

TABLE 4

| Solvent Capacity for Methane at 35° C. (lb $CH_4$/lb solvent) | | |
|---|---|---|
| Pressure, psia | BMDEG | DMEPG |
| 130.4 | $9.05 \times 10^{-4}$ | $1.03 \times 10^{-3}$ |
| 97.5 | $8.46 \times 10^{-4}$ | $7.71 \times 10^{-4}$ |
| 83.0 | $7.41 \times 10^{-4}$ | $6.71 \times 10^{-4}$ |
| 67.3 | $5.58 \times 10^{-4}$ | $5.31 \times 10^{-4}$ |
| 52.5 | $5.77 \times 10^{-4}$ | $4.17 \times 10^{-4}$ |

EXAMPLE 5

This example shows that in addition to having a higher carbonyl sulfide solvent capacity than the control commercial solvent, the solvent of the present invention has an unexpected catalytic activity toward the hydrolysis of carbonyl sulfide in the presence of water. The hydrolysis experiments were carried out in the same apparatus as used in Example 1 above. 300 ml of 4-4'-(oxydi-2,1-ethanediyl)bismorpholine solvent containing 2.5 wt% water was charged to a stainless steel vessel. A carbonyl sulfide containing gas (1% carbonyl sulfide and 99% carbon dioxide) was sparged through a 90 micron meter size filter element. The exit gas was monitored for carbon dioxide, carbonyl sulfide, and hydrogen sulfide as a function of the time until a more or less steady state for carbonyl sulfide was reached. The data is tabulated in Table 5. The percent removal of carbonyl sulfide is apparently dependent upon temperature, pressure and gas flow rate. However, the data indicates that a significant hydrolysis is catalyzed by the 4-4'(oxydi-2,1-ethanediyl)bismorpholine solvent.

TABLE 5

| | | COS Hydrolysis | | |
|---|---|---|---|---|
| Run # | I °C. | P, psia | Gas flow ml/min* | % COS removed |
| 1 | 30 | 30 | 150 | 35.5 |
| 2 | 30 | 30 | 300 | 30.0 |
| 3 | 30 | 150 | 150 | 57.5 |
| 4 | 30 | 150 | 300 | 44.4 |
| 5 | 55 | 30 | 150 | 23.0 |
| 6 | 55 | 30 | 300 | 19.5 |
| 7 | 55 | 150 | 150 | 47.0 |
| 8A | 55 | 150 | 300 | 37.5 |
| 8B | 55 | 150 | 300 | 40.0 |

*measured at 20° C. and 1 atm.

EXAMPLE 6

The heat of absorption of acidic gaseous components in a solvent are very important in determining the amount of energy required to regenerate the solvent for cyclic use. The present example shows the relative heats of absorption for carbon dioxide, hydrogen sulfide and carbonyl sulfide for one of the solvents of the present invention, 4-4'(oxydi-2,1-ethanediyl)bismorpholine and for the dimethyl ether of polyethylene glycol, a known commercial solvent. The data calculated in Table 6 below shows that the respective solvents are quite comparable in this attribute.

TABLE 6

| | Heats of Absorption in BTU/lb | |
|---|---|---|
| | BMDEG | DMEPG |
| $CO_2$ | 149 | 160 |
| $H_2S$ | 199 | 190 |
| COS | 139 | 88 |

The following examples demonstrate the solvent capabilities of 2,2'-oxybis(N,N-dimethylethanamine), also known as bis(dimethylaminoethyl)ether (BDMAEE).

EXAMPLE 7

BDMAEE and Dimethyl Ether of Polyethylene Glycol Solvent Capacities for $CO_2$ and $H_2S$ The solvent capacity was obtained as in previous Examples 1 and 2 at 80° F. (26.7° C.). Table 7 shows the results.

TABLE 7

| | Solvent Capacities For $CO_2/H_2S$ (lb/lb Solvent) at 26.7° C. | | |
|---|---|---|---|
| | | BDMAEE (MW = 160) | DMEPG (MW = 280) |
| $CO_2$ | 210 psia | 0.1425 | 0.09743 |
| | 227 | 0.1513 | 0.09853 |
| | 321 | 0.2599 | 0.1485 |
| $H_2S$ | 83.8 psia | 0.2635 | 0.1336 |
| | 95 | 0.3188 | 0.1518 |
| | 112 | — | 0.3291 |

The data shows that for both $CO_2$ and $H_2S$ the solvent of the present invention, BDMAEE, has 50 to 100% more capacity than the dimethyl ethers of polyethylene glycol.

EXAMPLE 8

BDMAEE and Dimethyl Ethers of Polyethylene Glycol (DMEPG) Solvent Capacities to $CH_4$ and $C_2H_6$ Hydrocarbon rejection is important for the solvent to be used in the natural gas acid gas applications. Co-adsorption of methane, ethane, and the like with $CO_2$ and $H_2S$ should be minimized. This example shows that BDMAEE has higher hydrocarbon solubilities than DMEPG. (Previously in Example 4, we showed that BMDEG and DMEPG have similar HC solubilities at 35° C.). This solvent is particularly well suited for the removal of acid gases from coal gas wherein $CH_4$ and $C_2H_6$ concentrations are small.

TABLE 8

| | Solvent Capacities For $CH_4$ and $C_2H_6$ (lb/lb solvent) at 26.7° C. | | |
|---|---|---|---|
| | | BDMAEE (MW = 160) | DMEPG (MW = 280) |
| $CH_4$ | 115 psia | $4.72 \times 10^{-3}$ | $1.33 \times 10^{-3}$ |
| | 265 | $1.20 \times 10^{-2}$ | $3.06 \times 10^{-3}$ |
| | 277 | $1.27 \times 10^{-2}$ | $3.20 \times 10^{-3}$ |
| $C_2H_6$ | 115 psia | $5.33 \times 10^{-2}$ | $1.47 \times 10^{-2}$ |
| | 247 | $1.35 \times 10^{-1}$ | $3.32 \times 10^{-2}$ |
| | 312 | $1.77 \times 10^{-1}$ | $4.29 \times 10^{-2}$ |

The solvents of the present invention have been shown to have high solvent capacity for $CO_2$, $H_2S$ and COS and specifically selectivity for $H_2S$ and COS over $CO_2$. Additionally, they have been shown to hydrolyze COS to $H_2S$ and $CO_2$ in the presence of water. The solvents of the present invention achieve these goals over a wide range of working conditions, such as pressures from ambient up to 2,000 psia, temperatures above the freezing point of the system of $-10°$ C. up to 200° C., preferably 0° to 100° C. and in dilution with water from 0 to 99.5 wt% preferably 30 to 90 wt%.

The solvents can be used in typical absorption/desorption purification processes wherein they are regenerated by heat, pressure reduction or alternately, an inert stripping gas. The selectivity of the solvent of the present invention for sulfur containing acid gases over $CO_2$ allows the solvents to be used economically for clean up of gas streams having high $CO_2$ content where normally it would be too expensive to treat the large volume of $CO_2$ extractable with a non-selective process. This factor, combined with the low heats of absorption (and therefore desorption) makes the solvents of the present invention particularly attractive for acid gas removal.

The solvents also have low vapor pressures over the normal range of scrubbing/regeneration and this factor provides the ability to use reduced solvent amounts with a reduction in the storage and makeup of the solvent over an extended period of operation. The solvent compounds can also be used in combination with other solvents or vehicles, preferably in a range of 5 to less than 100 wt% of said other solvent. A particularly effective solvent system comprises a predominant amount of 4-4'(oxydi-2,1-ethanediyl)bismorpholine with a viscosity reducing effective amount of 2-[2-(4-morpholinyl)ethoxy]ethanol. The amount of the latter component is preferably in the range of 5 to 40 wt%.

The present invention has been described with regard to several specific embodiments. However, it is believed that those skilled in the art can contemplate variations from the described embodiments which are deemed to be within the scope of the invention, which scope should be ascertained from the claims which follow.

We claim:

1. A process for purifying gas streams of acid gas components, comprising $H_2S$, COS and $CO_2$, and catalytically hydrolyzing any COS to $H_2S$ and $CO_2$, comprising contacting said gas stream in the presence of at least a minor amount of water with an acid gas absorbing solvent compound selected from the group having the formula:

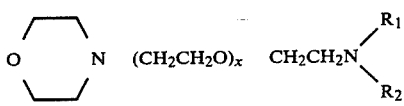

where $x = 1$, 2 or 3 and where $R_1$ and $R_2$ are individually lower alkyl of $C_1$ to $C_4$ normal or branched hydrocarbons or $R_1$ and $R_2$ form a cyclic derivative having the structure:

so as to absorb a predominant amount of such acid gas components from said gas stream.

2. The process of claim 1 wherein the compound is in solution with another solvent or vehicle and is in a concentration of 5 to less than 100 wt% of the other solvent.

3. The process of claim 1 wherein the compound is in a concentration of 30 to 90 wt% based on water.

4. The process of claim 1 wherein the acid gas containing absorbing solvent compound is separated from the gas stream and regenerated by a process selected from the group comprising; heating, reducing pressure or stripping with an inert gas or combinations of these processes.

5. The process of claim 4 wherein the regenerated absorbing solvent compound is recycled to contact the acid gas containing gas stream.

6. The process of claim 1 wherein the gas stream is contacted with the adsorbing solvent compound at a temperature of $-10°$ to $200°$ C. and a pressure of 15 to 2000 psia.

7. The process of claim 1 wherein the compound is 4-4'(oxydi-2,1-ethanediyl)bismorpholine.

8. The process of claim 7 wherein the solvent has a viscosity reducing effective amount of 2-[2-(4-morpholinyl)ethoxy]ethanol.

9. The process of claim 8 wherein the viscosity reductant is in a concentration of 5 to 40 wt% of the solvent compound.

10. A process for purifying gas streams of acid gas components, comprising $H_2S$, COS and $CO_2$, and catalytically hydrolyzing any COS to $H_2S$ and $CO_2$ comprising contacting said gas stream in the presence of at least a minor amount of water with an acid gas absorbing solvent compound selected from the group of 4,4'-(oxydi-2,1-ethenediyl)bismorpholine, 2-[2-(4-morpholinyl)ethoxy]ethanol, N,N-dimethyl-4-morpholineethanamine, and N,N-dimethyl-2-[2-(4-morpholinyl)ethoxy]ethanamine so as to absorb a predominant amount of such acid gas components from said gas stream.

* * * * *